(12) United States Patent
Li

(10) Patent No.: US 7,834,142 B2
(45) Date of Patent: Nov. 16, 2010

(54) SHORTENED GLUCAGON-LIKE PEPTIDE 1(SGLP-1) PREPARATION METHOD AND APPLICATION

(75) Inventor: Yuan Li, Dalian (CN)

(73) Assignee: Dalian D.N. Bio-Engineering Co., Ltd., Liaoning (CN)

( * ) Notice: Subject to any disclaimer, the term of this patent is extended or adjusted under 35 U.S.C. 154(b) by 604 days.

(21) Appl. No.: 11/665,277

(22) PCT Filed: Mar. 30, 2006

(86) PCT No.: PCT/CN2006/000562

§ 371 (c)(1),
(2), (4) Date: Apr. 11, 2007

(87) PCT Pub. No.: WO2007/056907

PCT Pub. Date: May 24, 2007

(65) Prior Publication Data

US 2009/0118172 A1    May 7, 2009

(30) Foreign Application Priority Data

Nov. 21, 2005    (CN) .................... 2005 1 0047801

(51) Int. Cl.
*C07K 14/605* (2006.01)
(52) U.S. Cl. .................... 530/324; 530/308; 514/12
(58) Field of Classification Search ............. 530/324, 530/399, 308; 514/12
See application file for complete search history.

(56) References Cited

U.S. PATENT DOCUMENTS 6,133,235 A * 10/2000 Galloway et al. ............. 514/12
6,268,343 B1 * 7/2001 Knudsen et al. .............. 514/12

FOREIGN PATENT DOCUMENTS

WO    2006005667    *  1/2006
WO    2006097537    *  9/2006

OTHER PUBLICATIONS

Li, Yuan, Journal of Peptide Science 14(7), 777-785, 2008.*

* cited by examiner

*Primary Examiner*—David Lukton
(74) *Attorney, Agent, or Firm*—Squire Sanders & Dempsey, LLP

(57) ABSTRACT

This invention relates to similar compound of glucagon-like peptide 1 (glucagon-like peptide-1, GLP-1) secreted by insulinotropic hormone, i.e. shortened glucagon-like peptide 1 (sGLP-1) consisting of 26 aminoacids. Its sequence is as follows: His-X1-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu (SEQ ID NO: 2). In comparison with the present GLP-1 and its similar compound, the shortened glucagon-like peptide 1 (sGLP-1) in this invention has the following prominent advantages: 1. After reconstruction, the shortened peptide chain has stronger simulation to islet cell captors and stronger insulin secretion stimulation action; 2. the reconstructed simulation sequence can resist dipeptidyl peptidase decomposition by change of the second aminoacid sequence from Ala to Gly or Ser to prolong its half time and enhance drug action; 3. To shorten the peptide chain leads to reduced synthesis cost.

7 Claims, 2 Drawing Sheets

Analytical Results Table

Figure 1:
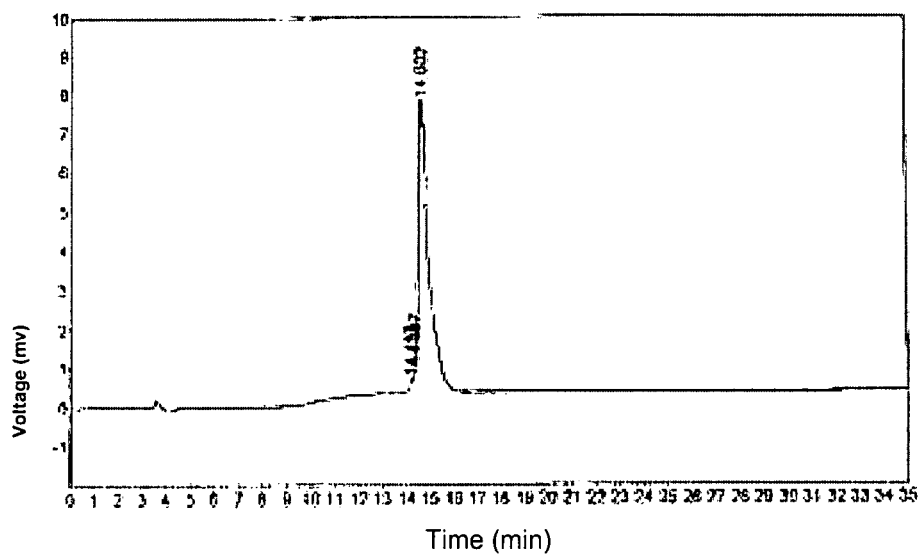

| Peak No. | Peak Name | Retaintion Time | Peak Height | Peak Area | Content |
|---|---|---|---|---|---|
| 1 | | 14.197 | 281.310 | 2298.333 | 0.9875 |
| 2 | | 14.387 | 567.292 | 3062.078 | 0.9875 |
| 3 | | 14.602 | 7375.989 | 227377.500 | 97.6968 |
| total | | | 8233.590 | 232737.911 | 100.0000 |

SEQUENCE LISTING

<160> NUMBER OF SEQ ID NOS: 10

<210> SEQ ID NO 1
<211> LENGTH: 30
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 26
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa is Gly or Ser

<400> SEQUENCE: 2

His Xaa Glu Gly Thr Phe Thr Ser Asp Val Ser Ser Tyr Leu Glu Gly
1               5                   10                  15

Gln Ala Ala Lys Glu Phe Ile Ala Trp Leu
            20                  25

<210> SEQ ID NO 3
<211> LENGTH: 26
<212> TYPE: PRT
<213> ORGANISM: Artificial Sequence
<220> FEATURE:
<223> OTHER INFORMATION: Synthetic peptide

<400> SEQUENCE: 3

His Gly Glu Gly Thr Phe Thr Ser Asp Val Ser Ser Tyr Leu Glu Gly
1               5                   10                  15

Gln Ala Ala Lys Glu Phe Ile Ala Trp Leu
            20                  25

<210> SEQ ID NO 4
<211> LENGTH: 26
<212> TYPE: PRT
<213> ORGANISM: Artificial Sequence
<220> FEATURE:
<223> OTHER INFORMATION: Synthetic peptide

<400> SEQUENCE: 4

His Ser Glu Gly Thr Phe Thr Ser Asp Val Ser Ser Tyr Leu Glu Gly
1               5                   10                  15

Gln Ala Ala Lys Glu Phe Ile Ala Trp Leu
            20                  25

<210> SEQ ID NO 5
<211> LENGTH: 30
<212> TYPE: PRT
<213> ORGANISM: Artificial Sequence
<220> FEATURE:
<223> OTHER INFORMATION: Synthetic peptide

<400> SEQUENCE: 5

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 6
<211> LENGTH: 23
<212> TYPE: PRT
<213> ORGANISM: Artificial Sequence
<220> FEATURE:
<223> OTHER INFORMATION: Synthetic peptide

<400> SEQUENCE: 6

His Ser Glu Gly Thr Phe Thr Ser Asp Val Ser Ser Tyr Leu Glu Gly
1               5                   10                  15

Gln Ala Ala Lys Glu Phe Ile
            20

<210> SEQ ID NO 7
<211> LENGTH: 23
<212> TYPE: PRT
<213> ORGANISM: Artificial Sequence
<220> FEATURE:
<223> OTHER INFORMATION: Synthetic peptide -continued

```
<400> SEQUENCE: 7

His Gly Glu Gly Thr Phe Thr Ser Asp Val Ser Ser Tyr Leu Glu Gly
1               5                   10                  15

Gln Ala Val Arg Leu Phe Ile
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic peptide

<400> SEQUENCE: 8

His Gly Glu Gly Thr Phe Thr Ser Asp Val Ser Ser Tyr Met Glu Glu
1               5                   10                  15

Glu Ala Val Arg
            20

<210> SEQ ID NO 9
<211> LENGTH: 14
<212> TYPE: PRT
<213> ORGANISM: Artificial Sequence
<220> FEATURE:
<223> OTHER INFORMATION: Synthetic peptide

<400> SEQUENCE: 9

His Gly Glu Gly Thr Phe Thr Ser Asp Val Ser Ser Tyr Met
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Synthetic peptide

<400> SEQUENCE: 10

His Gly Glu Gly Thr Phe Thr Ser Asp Val Ser Ser
1               5                   10
```

SHORTENED GLUCAGON-LIKE PEPTIDE 1(SGLP-1) PREPARATION METHOD AND APPLICATION

This application is a 371 of PCT/CN06/00562, filed Mar. 30, 2006, which claims foreign priority to CN 2005/10047801.4, filed Nov. 21, 2005.

FIELD OF THIS TECHNIQUE

This invention relates to similar compound of glucagon-like peptide 1(GLP-1) secreted by insulinotropic hormone as well as its preparation method and application.

BACKGROUND TECHNIQUE

In recent years, the research on GLP-1 and Exendin 4 has received much attention. Both of them have high homology, so they have good effect on application in Type II diabetes mellitus treatment. GLP-1 is a polypeptide separated and purified from human's intestinal tract, while Exendin 4 is a peptide extracted from venom in Mexican giant lizard. Both GLP-1 and Exendin 4 can promote pancreas to synthesize and secrete insulin in case of low concentration, further help diabetics control their blood glucose. GLP-1 is an intestinal tract incretion secreted by human, generated by proglucagon (Proglucagon) molecule under the action of intestinal tract proteolytic enzyme, and therefore called glucagon polypeptide. In case of the blood glucose level exceeding 6 mmol/L, GLP-1 can promote insulin secretion; while in case of blood glucose level back to normal value, no continuous action occurs, which is very useful to treat Type II diabetes mellitus. There are two kinds of GLP-1 in human body: one is GLP-1(7-36)$NH_2$, which is a polypeptide consisting of 30 aminoacid residues (namely the 7th to 36th aminoacids in proglucagon) with amidated End C; and the other is GLP-1(7-37), which is a polypeptide consisting of 31 aminoacid residues (namely the 7th to 37 the aminoacids in proglucagon). GLP-1(7-36)$NH_2$ and GLP-1(7-37) have the same insulinotropic hormone secretion action. The experiments prove that the interaction of GLP-1 and isolated pancreatic islet cells can promote its insulin secretion in case of the concentration between $1\times10^{-10}$ and $1\times10^{-11}$ mol/L, and therefore they are called insulinotropin. U.S. Pat. No. 5,424,286 opens comparative experiments of Exendin 4 and GLP-1 insulinotropic hormone secretion. In comparison with GLP-1, Exendin 4 concentration required for insulin secretion action regeneration is lower, and Exendin 4 has longer half time in human body. The research shows that GLP-1 or Exendin 4 may become a more ideal drug for Type II diabetes mellitus treatment.

An ideal drug for Type II diabetes mellitus treatment reduces fasting blood glucose level and postprandial blood glucose level, does not lead to low blood glucose level, reduces cardiovascular system deuteropathy, and does not other side reaction. GLP-1 is a peptide consisting of 30 aminoacids, and its sequence His-Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg (SEQ ID NO: 1). For diabetes mellitus treatment, this sequence has such advantages as natural sequence generated in human body, many features like the above, and few side reactions. For example, it can inhibit glucogen secretion, slow down stomach intestine evacuation, inhibit appetite for food, etc. In addition, GLP-1 receptor stimulation can also promote cell proliferation and regeneracy to increase insulin secretion and tolerance to sugar. But this sequence has such disadvantage: the first two aminoacids His-Ala are so fast decomposed by dipeptidyl peptidase on human body and deactivated that it has a very short half time only between 90 and 120 seconds in human body, and therefore it is almost useless in clinical treatment. There are a lot of research and patents on GLP-1 sequence reconstruction in China now, but GLP-1 sequence length is not reduced during its sequence reconstruction.

Exendin 4 has a long half time in human body and prominent blood glucose-lowering effect, but chemically synthesized Exendin 4 is a peptide consisting of 39 aminoacids, which has high cost, and as a heterogeny polypeptide, may induce human to generate antibody in case of long-term use, resulting in invalidation

INVENTION CONTENT

This invention aims to overcome the above defects and offers a shortened glucagon-like peptide 1(sGLP-1), which more strongly stimulates islet cell receptors, stimulates insulin secretion and prolongs its half time, as well as its preparation method with low synthesis cost and its application.

The technical proposal to realize the above mentioned purposes in this invention is to shorten the glucagon-like peptide 1(sGLP-1) to 26 aminoacid. Its sequence is as follows: His-X1-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu (SEQ ID NO: 2)

Abbreviations: His (abbreviated to: H, similarly hereinafter), Gly (G), Glu (E), Thr (T), Phe (F), Ser(S), Asp (D), Val (V), Tyr (Y), Leu (L), Gln (Q), Lys (K), Ile (I), and Trp (W).

Where X1 is Gly or Ser.

Shortened Glucagon-Like Peptide 1(sGLP-1) Preparation Method:

Step 1: sGLP-1 Peptide Resin Synthesis:

Weight 0.5 gram of polypeptide synthetic resin to a synthesis reaction column, and add dimethylformamide solvent to swell it. According to sGLP-1 aminoacid sequence, weight 0.1 gram of 9-pyrene methyl carbonyl and aminoacid for aminoacid End N (FMOC) protection to a reactor container, use Merrifield solid phase chemical synthesis method synthesize sGLP-1 peptide resin. sGLP-1 aminoacid sequence begins with End C. Add dimethylformamide-dissolved N,N'-Diisopropylcarbodiimide (DIC), 4-dimethylamino pyridine (DMAP) and the first aminoacid (FMOC-Leu) at End C to the synthesis reaction column for 2 or 3-hour reaction, decompress the column and remove all the reactant solution, wash the resin three times with isopropanol, dichloromethane and dimethylformamide respectively, and add dimethylformamide deprotection solution containing 20% (V/V) hexahydropyridine. After 30-minute reaction, remove the reaction solution, and wash it three times with isopropanol, dichloromethane and dimethylformamide respectively. After that, add the second aminoacid protected by FMOC, HOBt (anhydrous), HBTU and N,N-diisopropylethylamine (DIPEA) for 5-minute dissolution and activation, and then add them to the reactor for two-hour reaction. Wash the resin according to the above method, deprotect it. After that, couple reaction happens the according to sequence structure until the sequence completes. Wash it thoroughly with dimethylformamide to remove the residual uncoupled reagent, dry the peptide resin with inert gas $N_2$, and keep it standby.

Step 2: sGLP-1 Resin Lysis

Take the above peptide resin to a container, and add lysis solution containing 9.5 ml trifluoroacetic acid, 0.4 ml sulfo methyl phenate, 0.4 ml methyl phenate and 0.2 ml-1,2-dithioglycolfor two-hour reaction at room temperature without direct sunlight. After that, filter it to obtain the filtrate, and concentrate the filtrate at room temperature. Keep the filtrate to the frozen diethyl ether absolute for overnight, centrifuge it, discard the supernatant, dissolve the deposit with water or glacial acetic acid, freeze it, and dry it in freeze drier to obtain coarse peptide.

Step 3: sGLP-1 Peptide Purification

Dissolve the above coarse peptide with LAL reagent water to a sample solution, filter and collect the sample filtrate; filter acetonitrile and LAL reagent water with 0.45 u filter membrane respectively, add 0.1% trifluoroacetic acid to acetonitrile and LAL reagent water respectively, mix them well, and use C18 reversed-phase column for separation and purification. The separation conditions: mobile phase A: 0.1% trifluoroacetic acid+100% $H_2O$; mobile phase B: 0.1% trifluoroacetic acid+100% acetonitrile; 0→90 minute gradientelution and purification. Collect and freeze the purified sGLP-1 eluent, and dry it in the freeze drier to obtain pure sGLP-1 polypeptide product.

The shortened glucagon-like peptide 1(sGLP-1) in this invention is used as drug for Type II diabetes mellitus treatment, such as injection, tablet or capsule, and spray for Type II diabetes mellitus treatment.

In addition to sGLP-1, the injection contains sGLP-1 and the diluting liquid which human can accept, such as water for injection, normal saline and phosphate buffer solution; the tablet or capsule contains sGLP-1 and the stabilizer, shape-fixing agent, etc, compatible with drug.

In comparison with the present GLP-1 and its similar compound, the shortened glucagon-like peptide 1(sGLP-1) in this invention has the following prominent advantages: 1. After reconstruction, the shortened peptide chain has stronger binding power to islet cell captors and stronger insulin secretion stimulation action; 2. The reconstructed simulation sequence can resist dipeptidyl peptidase decomposition by change of the second aminoacid sequence from Ala to Gly or Ser to prolong its half time and enhance drug action; 3. To shorten the peptide chain leads to reduced synthesis cost. Polypeptide can generally be prepared by chemical synthesis and gene engineering technique. But the production cost is so high as to become a barrier to enter drug market. In the synthesize method in this invention, similar compound of polypeptide can be obtained by change of several aminoacids in the peptide chain and also produced on large-scale at low cost. The results of the model experiments on Type II diabetes mellitus rats and the blood glucose-lowering treatment experiments on diabetes mellitus models show that sGLP-1 in this invention has better blood glucose-lowering effect than GLP-1 and its reconstructed sequence, and the animal experiments show a prominently improved blood glucose-lowering effect. The combination of the reconstructed shortened sequence and islet cell captor leads to better insulin secretion stimulation effect, and better application prospect in drug for Type diabetes mellitus treatment.

DESCRIPTION OF ATTACHED FIGURES

Figure 2:
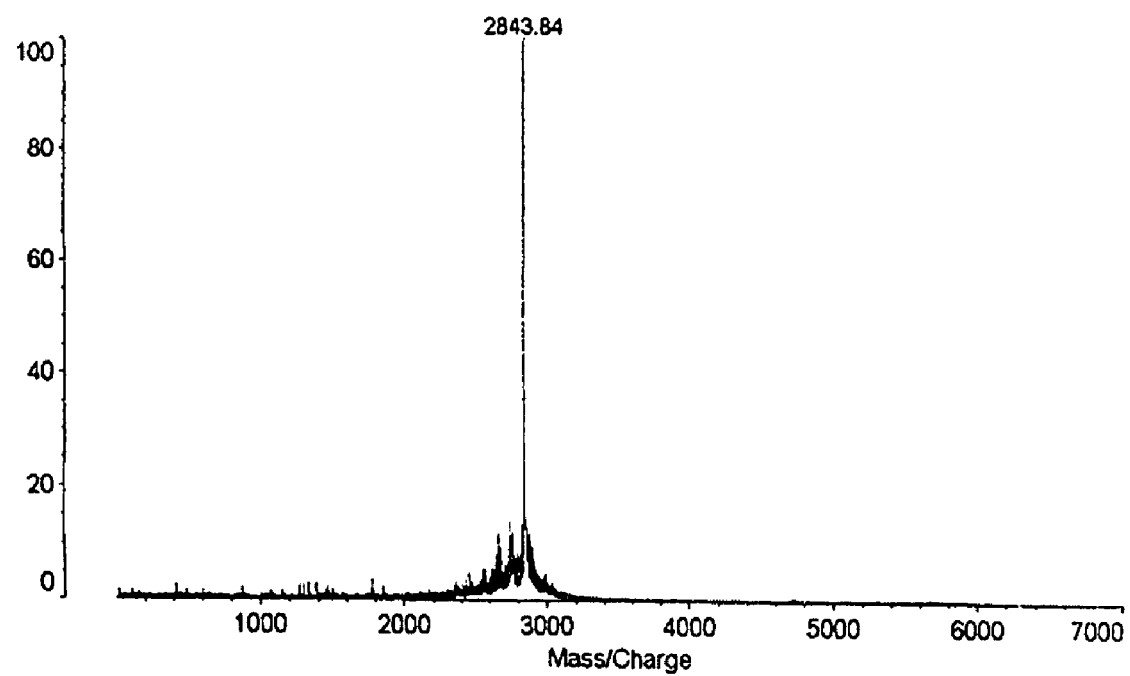

FIG. 1 is liquid chromatogram for sGLP-1 purity.
FIG. 2 is sGLP-1 molecule weight mass spectrogram.

EXECUTION EXAMPLES

Example 1 sGLP-1 synthesized according to the following method has the sequence as follows: His-Gly-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu (SEQ ID NO: 3)

Step 1: sGLP-1 Peptide Resin Synthesis:

Weight 0.5 gram of Wang resin (or other polypeptide synthetic resins) to a synthesis reaction column, and add dimethylformamide solvent to swell it. According to aminoacid sequence to reduce blood glucose peptide in this invention, weight 0.1 gram of 9-pyrene methyl carbonyl and aminoacid for aminoacid End N (FMOC) protection to a reactor container, and begin with End C according to Merrifield solid phase chemical synthesis method (the detailed method is as follows) and sGLP-1 aminoacid sequence in this invention. Add 4 ml of 10 ml dimethylformamide-dissolved N,N'-Diisopropylcarbodiimide (DIC), 0.012 gram of 4-dimethylamino pyridine (DMAP) and the first aminoacid (FMOC-Leu) at End C to the synthesis reaction column for 2 or 3-hour reaction, decompress the column and remove all the reactant solution, wash the resin three times with isopropanol, dichloromethane and dimethylformamide respectively, and add dimethylformamide deprotection solution containing 20% (V/V) hexahydropyridine. After 30-minute reaction, remove the reaction solution, and wash it three times with isopropanol, dichloromethane and dimethylformamide respectively. After that, add the second aminoacid protected by FMOC, 0.22 gram of HOBt (anhydrous), 0.6 gram of HBTU and 0.35 ml of N,N-diisopropylethylamine (DIPEA) for 5-minute dissolution and activation, and then add them to the reactor for two-hour reaction. Wash the resin according to the above method, deprotect it. After that, couple reaction happens the according to sequence structure until the sequence completes. Wash it thoroughly with dimethylformamide to remove the residual uncoupled reagent, dry the peptide resin with inert gas $N_2$, and keep it standby.

Step 2: sGLP-1 Resin Lysis:

Take the above peptide resin to a container, and add lysis solution containing 9.5 ml trifluoroacetic acid, 0.4 ml sulfo methyl phenate, 0.4 ml methyl phenate and 0.2 ml-1,2-dithioglycolfor two-hour reaction at room temperature without direct sunlight. After that, filter it to obtain the filtrate, and concentrate the filtrate at room temperature. Keep the filtrate to the frozen diethyl ether absolute for overnight, centrifuge it, discard the supernatant, dissolve the deposit with 200 ml water or glacial acetic acid, freeze it, and dry it in freeze drier to obtain coarse peptide.

Step 3: sGLP-1 Peptide Purification:

Dissolve the above coarse peptide with 200 ml LAL reagent water to a sample solution, filter and collect the sample filtrate; filter acetonitrile and LAL reagent water with 0.45 u filter membrane respectively, add 0.1% trifluoroacetic acid to acetonitrile and LAL reagent water respectively, mix them well, and use C 18 reversed-phase column for separation and purification. The separation conditions: mobile phase A: 0.1% trifluoroacetic acid+100% H$_2$O; mobile phase B: 0.1% trifluoroacetic acid+100% acetonitrile; 0→90 minute gradientelution and purification. Collect and freeze the purified sGLP-1 eluent, and dry it in the freeze drier to obtain pure sGLP-1 polypeptide product.

Example 2 sGLP-1 synthesized according to the following method has the sequence as follows: His-Ser-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu (SEQ ID NO: 4).

Animal Experiment:

1. Blood glucose-lowering effect experiment:

Material and Method

GK diabetes mellitus rats (Provided by Shanghai Laboratory Animal Center, Chinese Academy of Sciences)

sGLP-1 sequence is as follows:

```
No. 1:   HGEGTFTSDVSSYLEGQAAKEFIAWLVKGR    (SEQ ID NO: 5)

No. 2:   HGEGTFTSDVSSYLEGQAAKEFIAWL        (SEQ ID NO: 3)

No. 3:   HSEGTFTSDVSSYLEGQAAKEFIAWL        (SEQ ID NO: 4)

No. 4:   HSEGTFTSDVSSYLEGQAAKEFI           (SEQ ID NO: 6)

No. 5:   HGEGTFTSDVSSYLEGQAVRLFI           (SEQ ID NO: 7)

No. 6:   HGEGTFTSDVSSYMEEEAVR              (SEQ ID NO: 8)

No. 7:   HGE GTFTSDVSSYM                   (SEQ ID NO: 9)

No. 8:   HGEGTFTSDVSS                      (SEQ ID NO: 10)
```

The above eight polypeptides with different sequence is mixed with 0.9% NaCl solution to prepare 1 mg/ml solution, which is standby.

The rats are grouped at random, and fast overnight. Use graduated capillaries (treated with heparin before injection) to sample 20 microliters of blood from their orbital sinuses, add 300 microliters of normal saline to the blood and mix well, centrifuge it at 3000 rpm to remove erythrocyte, and use blood serum for fasting blood glucose level determination. Inject each group of rats with different polypeptides, and use normal saline as Control N. All the rats are injected at 0.1 mg/time, twice a day for two weeks. They must fast overnight, and be sampled according to the above method for fasting blood glucose level determination. The result is seen at Attached Table 1, No. 1 to No. 5 have blood glucose-lowering effect. No. 1 sequence is full-length GLP-1 sequence, in which the second aminoacid is changed from A to G, as Control P; No. 2 to No. 5 are the reconstructed sequences with different shortened length. No. 2 and No. 3 have blood glucose-lowering effect prominently exceeding No. 1, and therefore No. 2 and No. 3 are the sGLP-1 sequences finally determined in this invention.

2. Blood Glucose-Lowering Effect on NOD Mice

Experimental Material and Method:

NOD mice (Provided by Shanghai Laboratory Animal Center, Chinese Academy of Sciences) fasting overnight.

40% glucose, 0.9% NaCl solution, pure sGLP-1 product (Prepared in Example 1), pure GLP-1 product, reagent kit for blood glucose level determination (Made by Shanghai Institute of Biological Products (SIBP), Ministry of Health P.R.China.) NOD mice fast overnight, and are divided into three groups. Fasting Group 1 is injected with 200 microliters of 40% glucose and 10 microgram of sGLP-1; Fasting Group 2 is injected with 200 microliters of 40% glucose and 10 microgram of GLP-1; Group 3, a control group, is injected with only glucose. Immediately use graduated capillaries (treated with heparin before injection) to sample 20 microliters of blood from their orbital sinuses, add 300 microliters of normal saline to the blood and mix well, centrifuge it at 3000 rpm to remove erythrocyte, and use blood serum for fasting blood glucose level determination. Repeat the above operations at 30 minutes, 60 minutes and 120 minutes after that respectively. The blood serum of the three groups is determined on blood glucose level according to the method in the reagent kit in order to check the blood glucose-lowering effect of each group.

The result is shown in Table 1.

The blood glucose level of the control group greatly rises and then gradually falls back to normal level, while the blood glucose level of the administrated group does not rise significantly, and rests at normal level because of insulin secretion promotion after administration and avoidance of blood glucose level fluctuation. Thus, this can prove that sGLP-1 and GLP-1 have blood glucose-lowering effect.

TABLE 1 blood glucose-lowering effect of sGLP-1 on NOD mice

| | After administration | | | |
|---|---|---|---|---|
| | 0 minutes | 5 minutes | 10 minutes | 20 minutes |
| sGLP-1 | 4.08 | 4.34 | 4.28 | 3.98 |
| GLP-1 | 4.11 | 5.12 | 4.87 | 4.03 |
| Control group | 4.09 | 8.07 | 6.30 | 5.16 |

Note:
The blood glucose level is mmol/L in this table.

3. Insulinotropic Hormone Secretion Effect of sGLP-1

Experimental Material and Method:

NOD mice (Provided by Shanghai Laboratory Animal Center, Chinese Academy of Sciences)

0.9% NaCl solution, pure sGLP-1 product (prepared in Example 1), pure GLP-1 product, and radio immunity insulin determination reagent kit (Made by Shanghai Institute of Biological Products (SIBP), Ministry of Health P.R.China.) NOD mice are divided into three groups. Use graduated capillary (wash the inner walls of the capillaries with 1 mg/mL heparin and dry them) to sample 50 microliters of blood from their orbital sinuses first, and inject the three groups of fasting mice with 10 microgram of sGLP-1, 10 microgram of GLP-1 and 200 microliters of normal saline, and regard this time as zero. Repeat the above operation at 5, 10, 20 and 30 minutes after that respectively. Place all the blood samples in a centrifuge tube with 50 microliters of normal saline in it, mix them well, centrifuge them at 3000 rpm to remove erythrocyte, and determinate insulin level of blood serum according to the method in this radio immunity reagent kit to check insulinotropic hormone secretion effect of sGLP-1.

The experiment result is shown in Table 2. This result shows that sGLP-1 injected at fasting can prominently promote insulin secretion, and has the same short-time insulin generation stimulation capacity as GLP-1 and the medium and long-term insulin generation stimulation capacity stronger than GLP-1.

TABLE 2

Insulinotropic hormone secretion effect of sGLP-1

| | After administration | | | | |
|---|---|---|---|---|---|
| | 0 minutes | 5 minutes | 10 minutes | 20 minutes | 30 minutes |
| sGLP-1 | 2.88 | 10.56 | 19.88 | 24.67 | 16.45 |
| GLP-1 | 3.11 | 9.76 | 10.63 | 11.23 | 6.27 |
| Control group | 2.09 | 2.07 | 1.80 | 1.90 | 1.86 |

Note:
The insulin level is $10^{-6}$ international unit in this table.

4. C Peptide Secretion Promotion Effect of sGLP-1

Experiment Material and Method:
Healthy C57/BL mice (Provided by Shanghai Laboratory Animal Center, Chinese Academy of Sciences)
0.9% NaCl solution, pure sGLP-1 product (Prepared in Example 1), pure GLP-1 product.
Radio immunity C-peptide determination reagent kit (Made by Shanghai Institute of Biological Products (SIBP), Ministry of Health P.R.China.)
Healthy C57/BL mice are divided into three groups. Use graduated capillary (wash the inner walls of the capillaries with 1 mg/mL heparin and dry them) to sample 50 microliters of blood from their orbital sinuses first, and inject the three groups of fasting mice with 10 microgram of sGLP-1, 10 microgram of GLP-1 and 200 microliters of normal saline, and regard this time as zero. Repeat the above operation at 5, 10, 20 and 30 minutes after that respectively. Place all the blood samples in a centrifuge tube with 50 microliters of normal saline in it, mix them well, centrifuge them at 3000 rpm to remove erythrocyte, and determinate C peptide level of blood serum according to the method in this radio immunity reagent kit to check C peptide secretion promotion effect of sGLP-1.

The experiment result is shown in Table 3. This result shows that sGLP-1 injected at fasting can prominently promote c peptide secretion, and has the c peptide secretion promotion capacity exceeding GLP-1

TABLE 3

Insulinotropic hormone secretion effect of sGLP-1

| | After administration | | | | |
|---|---|---|---|---|---|
| | 0 minutes | 5 minutes | 10 minutes | 20 minutes | 30 minutes |
| sGLP-1 | 0.07 | 0.08 | 0.20 | 0.16 | 0.15 |
| GLP-1 | 0.07 | 0.08 | 0.15 | 0.11 | 0.09 |
| Control group | 0.07 | 0.06 | 0.08 | 0.06 | 0.06 |

Note:
The c peptide level is pmol/mL in this table.

The invention claimed is:

1. A peptide consisting of an amino acid sequence of: His-X1-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu (SEQ ID NO: 2) wherein X1 is Gly or Ser.

2. The peptide according to claim 1, wherein X1 is Ser.

3. A composition for treating Type II diabetes mellitus, comprising the peptide according to claim 1 and a carrier.

4. The composition of claim 3 in a formulation selected from injection formulation, tablet or capsule, and spray.

5. The composition according to claim 4, wherein the injection formulation contains a pharmaceutically acceptable carrier selected from water for injection, saline and phosphate buffer solution.

6. The composition according to claim 4, wherein the tablet or capsule further contains a pharmaceutically acceptable stabilizer or shape-fixing agent.

7. The peptide according to claim 1, wherein X1 is Gly.

* * * * *